United States Patent [19] [11] 4,139,363
Ziman [45] Feb. 13, 1979

[54] THIATRIAZOLIDIN-4-ONE-2-OXIDE HERBICIDES

[75] Inventor: Stephen D. Ziman, San Francisco, Calif.

[73] Assignee: Chevron Research Company, San Francisco, Calif.

[21] Appl. No.: 855,657

[22] Filed: Nov. 29, 1977

[51] Int. Cl.² ............... A01N 9/14; A01N 21/02; C07D 285/00
[52] U.S. Cl. ............................ 71/91; 260/302 R; 260/554
[58] Field of Search ............... 260/302 R; 71/91

[56] References Cited
U.S. PATENT DOCUMENTS

| 3,737,434 | 6/1973 | Hester | 71/91 |
| 3,900,484 | 8/1975 | Chupp | 71/91 |
| 4,013,447 | 3/1977 | Kay | 71/91 |

OTHER PUBLICATIONS

Huisgen et al., Ann., vol. 658, pp. 169–180, (1962).

Primary Examiner—Alton D. Rollins
Attorney, Agent, or Firm—D. A. Newell; T. G. DeJonghe; Raymond Owyang

[57] ABSTRACT

Novel 2,3,5-trisubstituted-1,2,3,5-thiatriazolidin-4-one-2-oxides have been found to have herbicidal activity. These 1,2,3,5-thiatriazolidin-4-one-2-oxides are prepared by reacting an N-aminourea (semicarbazide) and thionyl chloride.

18 Claims, No Drawings

THIATRIAZOLIDIN-4-ONE-2-OXIDE HERBICIDES

DESCRIPTION OF THE PRIOR ART

U.S. Pat. No. 3,900,484, issued Aug. 19, 1975, to John Paul Chupp, discloses the preparation of herbicidal 1,2,3,5-oxathiadiazolin-4-one-2-oxides by the reaction of an N-alkyl-N-hydroxy-N'-aryl urea and thionyl chloride.

Huisgen et al, *Annalen*, 658, 174 (1962) disclose the preparation of 2,3,5-triphenyl-2,3-dihydro-1,3,4-thiadiazol-1-one by the reaction of (alpha-anilino-benzal)-phenylhydrazine and thionyl chloride.

U.S. Pat. No. 3,925,054, issued Dec. 9, 1975, to John Kremner, discloses the preparation of 1,2,4-triazolidin-3-ones by the reaction of 2-alkyl-4-arylsemicarbazides and formaldehyde.

DESCRIPTION OF THE INVENTION

The 1,2,3,5-thiatriazolidin-4-one-2-oxide compounds of the invention may be represented by the following formula (I):

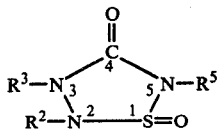

wherein $R^2$, $R^3$ and $R^5$ individually are alkyl of 1 to 6 carbon atoms; phenyl, naphthyl; or phenyl or naphthyl substituted with 1 to 3 substituents selected from fluoro, chloro, bromo, iodo, alkoxy of 1 to 4 carbon atoms and alkyl of 1 to 4 carbon atoms or one substituent selected from trifluoromethyl, trichloromethyl, tribromomethyl, phenoxy, or phenoxy substituted with 1 to 2 fluoro, chloro, bromo or alkyl of 1 to 4 carbon atoms.

Preferably $R^2$ is alkyl of 1 to 6 carbon atoms, and more preferably alkyl of 1 to 3 carbon atoms.

Preferably $R^3$ is alkyl of 1 to 6 carbon atoms, phenyl or phenyl substituted with 1 to 2 fluoro, chloro, bromo, alkyl of 1 to 4 carbon atoms or alkoxy of 1 to 4 carbon atoms, and more preferably alkyl of 1 to 3 carbon atoms, phenyl or phenyl substuted with 1 to 2 fluoro, chloro or bromo.

Preferably $R^5$ is alkyl of 1 to 6 carbon atoms, phenyl or phenyl substituted with 1 to 2 fluoro, chloro, bromo, alkyl of 1 to 4 carbon atoms or alkoxy of 1 to 4 carbon atoms, and more preferably alkyl of 1 to 3 carbon atoms, phenyl or phenyl substituted with 1 to 2 fluoro, chloro or bromo.

Representative alkyl groups which $R^2$, $R^3$ and $R^5$ may represent include methyl, ethyl, isopropyl, n-butyl and n-hexyl. Representative aryl groups which $R^3$ and $R^5$ may represent include 1-naphthyl, 2-naphthyl, 2-methyl-1-naphthyl, 4-chloro-1-naphthyl, 2,4-dichloro-1-naphthyl, 2-fluorophenyl, 3-chlorophenyl, 3-(4-chlorophenoxy)phenyl, 2-phenoxyphenyl, 2,4,5-trichlorophenyl, 4-tolyl, 3,5-dimethylphenyl, 4-trichloromethylphenyl, 2-tribromomethylphenyl, 2-methoxyphenyl, 4-ethoxyphenyl and 2-methyl-4-chlorophenyl.

In the compounds of formula (I), it is generally preferred that one of $R^2$, $R^3$ or $R^5$ is aryl (e.g., phenyl, naphthyl, or substituted phenyl or naphthyl), and two of $R^2$, $R^3$ or $R^5$ are alkyl.

A preferred class of compounds of formula (I) is that wherein $R^2$ is alkyl of 1 to 3 carbon atoms, $R^3$ is phenyl or phenyl substituted with 1 to 2 fluoro, chloro or bromo and $R^5$ is alkyl of 1 to 3 carbon atoms. Another preferred class of compounds is that wherein $R^2$ is alkyl of 1 to 3 carbon atoms, $R^3$ is alkyl of 1 to 3 carbon atoms and $R^5$ is phenyl or phenyl substituted with 1 to 2 fluoro, chloro or bromo.

Representative compounds of formula (I) include:

2,3-dimethyl-5-tolyl-1,2,3,5-thiatriazolidin-4-one-2-oxide 2-methyl-1-naphthyl-5-ethyl-1,2,3,5-thiatriazolidin-4-one-2-oxide 2-phenyl-3,5-dimethyl-1,2,3,5-thiatriazolidin-4-one-2-oxide 2,3-diethyl-5-(3,5-dichlorophenyl)-1,2,3,5-thiatriazolidin-4-one-2-oxide 2-hexyl-3,5-diphenyl-1,2,3,5-thiatriazolidin-4-one-2-oxide 2-(2-naphthyl)-3,5-dimethyl-1,2,3,5-thiatriazolidin-4-one-2-oxide 2-methyl-3-(2-trichloromethylphenyl)-5-methyl-1,2,3,5-thiatriazolidin-4-one-2-oxide 2-(4-phenoxyphenyl-3,5-dimethyl-1,2,3,5-thiatriazolidin-4-one-2-oxide 2,3,5-trimethyl-1,2,3,5-thiatriazolidin-4-one-2-oxide, and 2,3,5-triphenyl-1,2,3,5-thiatriazolidin-4-one-2-oxide The 1,2,3,5-thiatriazolidin-4-one-2-oxide compounds of the invention are prepared by reacting thionyl chloride and an N-aminourea (semicarbazide) (II) as depicted by the following reaction (1):

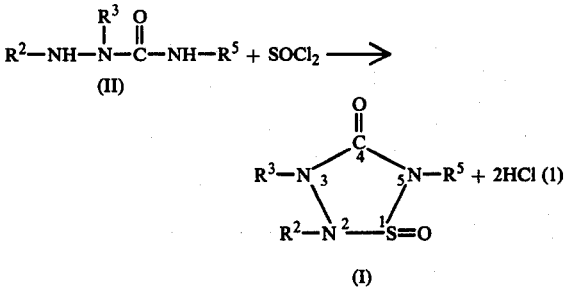

wherein $R^2$, $R^3$ and $R^5$ have the same significance as previously defined.

Preferably reaction (1) is conducted in the presence of a base. Suitable bases include inorganic bases such as alkali metal carbonates and bicarbonates, e.g., sodium carbonate and potassium bicarbonate, and organic bases, such as trialkyl amines, e.g., tributyl amine, and pyridine compounds, e.g., pyridine and dimethylpyridine. The preferred bases are pyridine compounds, particularly pyridine.

The precise mechanism and the reaction intermediates involved in reaction (1) are not known with certainty. However, it appears that the stoichiometry of the reaction is one mol of thionyl chloride per mol of N-aminourea. Therefore, substantially equimolar amounts of N-aminourea to thionyl chloride are employed, e.g., molar ratios of N-aminourea to thionyl chloride vary from about 1:1 to 1:1.5, although molar ratios of 1:1 to 1:1.1 are preferred. When a base is employed in the reaction, it is generally preferred to use enough base to scavenge the hydrogen chloride produced in the reaction. Therefore, molar ratios of base to thionyl chloride generally vary from about 2:1 to 2.4:1, although molar ratios varying from about 2:1 to 2.2:1 are preferred.

Generally the reaction is accomplished by reacting the N-aminourea, thionyl chloride and base in an inert liquid diluent. Suitable inert diluents include alkanes and haloalkanes, such as hexane, isooctane or dichloromethane, and aromatic compounds, such as benzene, toluene or chlorobenzene. Generally the amount of diluent employed ranges from 1 to 50 mols per mol of N-aminourea.

The reaction is suitably conducted at a temperature of from about −10° C. to 100° C., although temperatures of from about 0° C. to 75° C. are preferred. The reaction is conducted at or above atmospheric pressure. The reaction time will, of course, vary depending on the reaction temperature and the particular N-aminourea reactant employed. Generally, however, the reaction time varies from about 1 hour to 50 hours. The 1,2,3,5-thiatriazolidin-4-one-2-oxide product is isolated from the reaction mixture by conventional procedures, e.g., extraction, chromatography, crystallization, etc.

EXAMPLES

Example 1 — Preparation of 2,3-dimethyl-5-phenyl-1,2,3,5-thiatriazolidin-4-one-2-oxide A 2.75 g (0.032 mol) sample of thionyl chloride was added dropwise to a cooled (0° C.) solution of 4.18 g (0.023 mol) 2,3-dimethyl-4-phenylsemicarbazide and 3.62 g (0.046 mol) pyridine in 250 ml chloroform. The resulting reaction mixture was stirred at about 25° C. for about 16 hours, washed twice with water, dried over magnesium sulfate and evaporated under reduced pressure to give a yellow solid. The solid was recrystallized from hexane/benzene to give the product, as a white solid, m.p. 77–79° C. The infrared spectrum of the product showed a strong carbonyl absorption band at 5.78 micron. The nuclear magnetic resonance (NMR) spectrum of the product showed two 3-proton singlets (methyl protons) at 3.00 ppm and 3.26 ppm ppm and a 5-proton singlet (aromatic protons) at 7.43 ppm (relative to tetramethylsilane). The product is tabulated in Table I as Compound No. 1.

Example 2 — Preparation of 2,3-dimethyl-5-(4-chlorophenyl)-1,2,3,5-thiatriazolidin-4-one-2-oxide A slurry of 10 g (0.075 mol) 1,2-dimethylhydrazine hydrochloride and 15.2 g (0.15 mol) triethylamine in 300 ml dichloromethane was stirred until the hydrochloride salt dissolved. A solution of 4-chlorophenylisocyanate in dichloromethane was then added dropwise and the resulting solution was stirred at about 25° C. for about 2 days. The reaction mixture was washed with water, dried over magnesium sulfate and evaporated under reduced pressure to give 2,3-dimethyl-4-(4-chlorophenyl)-semicarbazide, as a white crystalline solid.

A solution of 8.13 g (0.068 mol) thionyl chloride in dichloromethane was slowly added to a cooled (0° C.) solution of 14.6 g (0.068 mol) 2,3-dimethyl-4-(4-chlorophenyl)semicarbazide and 10.8 g (0.136 mol) pyridine in 250 ml dichloromethane. The resulting reaction mixture was allowed to warm to about 25° C., stirred for about 16 hours, washed with water, dried over magnesium sulfate and evaporated under reduced pressure to give a tan liquid which slowly crystallized. Recrystallization of the crude product from hexane/benzene gave 14.7 g of the 2,3-dimethyl-5-(4-chlorophenyl)-1,2,3,5-thiatriazolidin-4-one-2-oxide product, as pink crystals, m.p. 83°–85° C. The nuclear magnetic resonance spectrum of the product showed 3-proton singlets (methyl protons) at 3.00 ppm and 3.26 ppm and a 4-proton singlet (aromatic protons) at 7.46 ppm (relative to tetramethylsilane). The product is tabulated in Table I as Compound No. 2.

Example 3 — Preparation of 2,5-dimethyl-3-phenyl-1,2,3,5-thiatriazolidin-4-one-2-oxide A 5.7-g (0.1-mol) sample of methyl isocyanate was added dropwise to a solution of 15.0 g (0.1 mol) 1-acetyl-2-phenyl-hydrazine and 2 drops triethylamine in 200 ml dichloromethane. The resulting reaction mixture was stirred for 2 hours at about 25° C., refluxed for about 16 hours and evaporated under reduced pressure to give 21 g of crude 1-acetyl-2-phenyl-4-methyl semicarbazide, as a yellow solid.

A mixture of 17 g (0.082 mol) of the semicarbazide prepared above, 14.2 g (0.1 mol) methyl iodide, 14.0 g (0.1 mol) potassium carbonate, and 200 ml ethanol was refluxed for 2 hours, cooled, filtered and evaporated under reduced pressure. The resulting residue was diluted with dichloromethane, filtered to remove suspended solids, washed with water, dried over magnesium sulfate, and evaporated under reduced pressure to give 10 g of crude 1-acetyl-1,4-dimethyl-2-phenyl-semicarbazide.

The 10-g sample of semicarbazide prepared above and 110 ml 37% hydrochloric acid were heated at 50° C. for 1 hour. The reaction mixture was then poured onto ice, neutralized to pH 7 with aqueous sodium hydroxide solution and evaporated under reduced pressure to give a yellow liquid. NMR spectroscopic analysis of the yellow liquid showed the presence of the starting semicarbazide. Therefore, the yellow liquid was redissolved in water, acidified with 10% hydrochloric acid and extracted with methylene chloride to remove the starting semicarbazide. The aqueous solution was then neutralized with sodium hydroxide and evaporated under reduced pressure to give 3.3 g of crude 1,4-dimethyl-2-phenylsemicarbazide.

A 2.2-g (0.0184-mol) sample of thionyl chloride was added slowly to a cooled (0° C.) solution of the 3.3-g (0.0184-mol) sample of semicarbazide prepared above and 2.9 g (0.036 mol) pyridine in 200 ml dichloromethane and then stirred at about 25° C. for 16 hours. The reaction mixture was washed with water, dilute hydrochloric acid, dried over magnesium sulfate and evaporated under reduced pressure to give a red oil, which was purified by filtration through silica gel to give the 2,5-dimethyl-3-phenyl-1,2,3,5-thiatriazine-1,4-dione product as an orange oil. The NMR spectrum of the product showed two 3-proton singlets at 2.96 ppm and 3.20 ppm and the aromatic protons as a multiplet at 7.13–7.90 ppm (relative to tetramethylsilane). The product is tabulated in Table I as Compound No. 4.

Other compounds of the invention were prepared by procedures similar to those of Examples 1–3. These compounds are reported in Table I. The structures of the compounds reported in Table I were verified by infrared spectroscopy and/or NMR analysis. All 1,2,3,5-thiatriazolidin-4-one-2-oxide compounds of the invention showed a strong carbonyl absorption band at about 5.86 micron.

UTILITY

The compounds of the present invention are herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 0.2 to 60 kg/ha, and the preferred rate is in the range 0.5 to 40 kg/ha.

Pre-emergent herbicidal tests on representative compounds of the invention were made using the following method:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 micrograms/cm$^2$ (3 lbs/acre). The pot was watered and placed in a greenhouse. The pot was watered intermittently and was observed for seedling emergence, healt of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 mcg/cm$^2$ (3 lbs/acre). After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

TABLE I: COMPOUNDS OF FORMULA (I)

| No. | R$^2$ | R$^3$ | R$^5$ | m.p., °C | Sulfur Analysis, % Calc. | Found |
|---|---|---|---|---|---|---|
| 1 | CH$_3$ | CH$_3$ | φ | 76–79 | 14.2 | 14.2 |
| 2 | CH$_3$ | CH$_3$ | 4-Cl-φ | 83–85 | 12.4 | 12.6 |
| 3 | CH$_3$ | CH$_3$ | 3-CF$_3$-φ | 90–92 | 10.9 | 10.4 |
| 4 | CH$_3$ | φ | CH$_3$ | oil | 14.2 | 14.5 |
| 5 | CH$_3$ | CH$_3$ | 2-F-φ | 72–74 | 13.2 | 13.5 |
| 6 | CH$_3$ | CH$_3$ | 3-CH$_3$-C-φ | 59–62 | 12.6 | 12.6 |
| 7 | CH$_3$ | CH$_3$ | 3,4-Cl$_2$-φ | 104–106 | 10.9 | 11.0 |
| 8 | CH$_3$ | CH$_3$ | 4-φ-O-φ | 87–88 | 10.1 | 10.3 |
| 9 | CH$_3$ | φ | i-C$_3$H$_7$ | oil | 12.6 | 12.2 |
| 10 | CH$_3$ | 2-F-φ | CH$_3$ | oil | 13.2 | 13.9 |
| 11 | CH$_3$ | CH$_3$ | 4-F-φ | 89–90 | 13.2 | 13.6 |
| 12 | CH$_3$ | CH$_3$ | 2,6-Cl$_2$-φ | 106–108 | 10.9 | 10.8 |
| 13 | CH$_3$ | 4-CH$_3$O-φ | CH$_3$ | oil | 12.6 | 14.6 |
| 14 | CH$_3$ | 4-CH$_3$O-φ | i-C$_3$H$_7$ | oil | 11.3 | 10.9 |
| 15 | CH$_3$ | 3,4-Cl$_2$-φ | CH$_3$ | 147–149 | 10.9 | 10.9 |
| 16 | CH$_3$ | i-C$_3$H$_7$ | 3,4-Cl$_2$-φ | 62–65 | 9.9 | 9.2 |
| 17 | CH$_3$ | CH$_3$ | 3,4-(CH$_3$)$_2$-φ | oil | 12.6 | 12.8 |
| 18 | CH$_3$ | CH$_3$ | 2,6-(CH$_3$)-φ | 73–75 | 12.67 | 13.0 |
| 19 | CH$_3$ | CH$_3$ | 4-i-C$_3$H$_7$-φ | 135–136 | 11.8 | 11.7 |
| 20 | CH$_3$ | CH$_3$ | 2,4,5-Cl$_3$-φ | 152–154 | 9.7 | 9.7 |
| 21 | CH$_3$ | CH$_3$ | 4-n-C$_4$H$_9$-φ | oil | 11.4 | 10.8 |
| 22 | CH$_3$ | CH$_3$ | 2-naphthyl | 93–94 | 11.6 | 11.7 |
| 23 | i-C$_3$H$_7$ | φ | CH$_3$ | oil | 12.6 | 13.5 |
| 24 | CH$_3$ | CH$_3$ | 4-I-φ | 111–112 | 9.1 | 10.3 |
| 25 | CH$_3$ | CH$_3$ | 4-Br-φ | 101–103 | 10.5 | 10.8 |

TABLE II

| No. | Herbicidal Effectiveness at 3 lbs/acre -- Pre/Post | | | | | |
|---|---|---|---|---|---|---|
| | L | M | P | C | W | O |
| 1 | 0/93 | 0/95 | 0/70 | 0/25 | 0/25 | 0/20 |
| 2 | 0/100 | 0/100 | 0/84 | 0/50 | 0/80 | 0/55 |
| 3 | 0/75 | 0/90 | 0/20 | 0/0 | 0/0 | 0/40 |
| 4 | 100/100 | 100/100 | 100/90 | 97/0 | 90/55 | 100/40 |
| 5 | 30/100 | 30/100 | 15/100 | 0/30 | 0/75 | 0/80 |
| 6 | 0/90 | 0/100 | 0/95 | 0/0 | 0/15 | 0/0 |
| 7 | 98/100 | 58/100 | 98/100 | 0/93 | 0/75 | 0/83 |
| 8 | 0/65 | 15/ | 0/65 | 0/45 | 0/20 | 0/35 |
| 9 | 65/25 | 60/25 | 20/25 | 50/0 | 0/0 | 0/0 |
| 10 | 95/100 | 95/100 | 100/98 | 74/25 | 84/10 | 69/0 |
| 11 | 0/100 | 0/ | 0/100 | 0/85 | 0/85 | 0/85 |
| 12 | 0/0 | 0/ | 0/15 | 0/10 | 0/10 | 0/25 |
| 13 | 65/95 | 65/ | 95/80 | 55/65 | 45/50 | 20/85 |
| 14 | 0/20 | 0/ | 0/20 | 0/10 | 0/10 | 0/10 |
| 15 | 100/100 | 95/100 | 100/100 | 97/80 | 83/97 | 25/80 |
| 16 | 0/95 | 0/100 | 0/97 | 0/60 | 0/80 | 0/75 |
| 17 | 0/40 | 0/100 | 0/25 | 0/25 | 0/25 | 0/20 |
| 18 | 25/0 | 25/0 | 25/0 | 0/0 | 15/0 | 0/0 |
| 19 | 0/100 | 0/100 | 0/100 | 0/45 | 0/85 | 0/35 |
| 20 | 0/100 | 0/100 | 0/65 | 0/50 | 0/90 | 0/25 |

TABLE II-continued

| | Herbicidal Effectiveness at 3 lbs/acre — Pre/Post | | | | | |
|---|---|---|---|---|---|---|
| No. | L | M | P | C | W | O |
| 21 | 0/40 | 0/80 | 0/10 | 0/60 | 0/65 | 0/50 |
| 22 | 0/85 | 0/100 | 0/70 | 0/50 | 0/50 | 0/40 |
| 23 | 10/75 | 10/45 | 10/25 | 0/0 | 0/0 | 0/0 |
| 24 | 0/80 | 0/85 | 0/75 | 0/35 | 0/40 | 0/50 |
| 25 | 0/97 | 0/97 | 0/95 | 0/40 | 0/65 | 0/80 |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

What is claimed is:

1. A compound of the formula

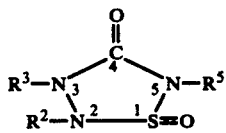

(I)

wherein $R^2$, $R^3$ and $R^5$ individually are alkyl of 1 to 6 carbon atoms; phenyl, naphthyl; or phenyl or naphthyl substituted with 1 to 3 of the same or different substituents selected from fluoro, chloro, bromo, iodo, alkoxy of 1 to 4 carbon atoms and alkyl of 1 to 4 carbon atoms or 1 substituent selected from trifluoromethyl, trichloromethyl or tribromomethyl, phenoxy, phenoxy substituted with 1 to 2 fluoro, chloro, bromo or alkyl of 1 to 4 carbon atoms.

2. The compound of claim 1 wherein one of $R^3$ or $R^5$ is phenyl, naphthyl, or phenyl or naphthyl substituted with 1 to 3 of the same or different substituents selected from fluoro, chloro, bromo, iodo, alkoxy of 1 to 4 carbon atoms and alkyl of 1 to 4 carbon atoms or 1 substituent selected from trifluoromethyl, trichloromethyl or tribromomethyl, phenoxy, phenoxy substituted with 1 to 2 fluoro, chloro, bromo or alkyl of 1 to 4 carbon atoms and two of $R^2$, $R^3$ or $R^5$ are alkyl.

3. The compound of claim 2 wherein $R^3$ and $R^5$ individually are alkyl of 1 to 6 carbon atoms, phenyl, or phenyl substituted with 1 to 2 fluoro, chloro, bromo, or alkyl of 1 to 4 carbon atoms.

4. The compound of claim 3 wherein $R^2$, $R^3$ and $R^5$ individually are alkyl of 1 to 3 carbon atoms, phenyl or phenyl substituted with 1 to 2 fluoro, chloro or bromo.

5. The compound of claim 4 wherein $R^2$ is alkyl of 1 to 3 carbon atoms, $R^3$ is phenyl or phenyl substituted with 1 to 2 fluoro, chloro or bromo, and $R^5$ is alkyl of 1 to 3 carbon atoms.

6. The compound of claim 5 wherein $R^2$ is methyl, $R^3$ is phenyl and $R^5$ is methyl.

7. The compound of claim 4 wherein $R^2$ is alkyl of 1 to 3 carbon atoms, $R^3$ is alkyl of 1 to 3 carbon atoms, and $R^5$ is phenyl or phenyl substituted with 1 to 2 fluoro, chloro or bromo.

8. The compound of claim 7 wherein $R^2$ is methyl, $R^3$ is methyl and $R^5$ is 3,4-dichlorophenyl.

9. A method for the control of undesirable vegetation which comprises applying to said vegetation or its habitat an herbicidally effective amount of a compound of the formula defined in claim 1.

10. An herbicidal composition comprising a biologically inert carrier and an herbicidally effective amount of a compound of the formula defined in claim 1.

11. A method of preparing a compound of the formula defined in claim 1 which comprises reacting substantially equimolar amounts of thionyl chloride and a compound of the formula $R^2NHN(R^3)CONHR^5$ wherein $R^2$, $R^3$ and $R^5$ are as defined in claim 1.

12. The method of claim 9 wherein one of $R^3$ or $R^5$ is phenyl, naphthyl, or phenyl or naphthyl substituted with 1 to 3 of the same or different substituents selected from fluoro, chloro, bromo, iodo, alkoxy of 1 to 4 carbon atoms and alkyl of 1 to 4 carbon atoms or 1 substituent selected from trifluoromethyl, trichloromethyl or tribromomethyl, phenoxy, phenoxy substituted with 1 to 2 fluoro, chloro, bromo or alkyl of 1 to 4 carbon atoms and two of $R^2$, $R^3$ or $R^5$ are alkyl.

13. The method of claim 12 wherein $R^3$ and $R^5$ individually are alkyl of 1 to 6 carbon atoms, phenyl, or phenyl substituted with 1 to 2 fluoro, chloro, bromo, or alkyl of 1 to 4 carbon atoms.

14. The method of claim 13 wherein $R^2$, $R^3$, and $R^5$ individually are alkyl of 1 to 3 carbon atoms, phenyl or phenyl substituted with 1 to 2 fluoro, chloro or bromo.

15. The method of claim 14 wherein $R^2$ is alkyl of 1 to 3 carbon atoms, $R^3$ is phenyl or phenyl substituted with 1 to 2 fluoro, chloro or bromo, and $R^5$ is alkyl of 1 to 3 carbon atoms.

16. The method of claim 15 wherein $R^2$ is methyl, $R^3$ is phenyl and $R^5$ is methyl.

17. The method of claim 14 wherein $R^2$ is alkyl of 1 to 3 carbon atoms, $R^3$ is alkyl of 1 to 3 carbon atoms, and $R^5$ is phenyl or phenyl substituted with 1 to 2 fluoro, chloro or bromo.

18. The method of claim 17 wherein $R^2$ is methyl, $R^3$ is methyl and $R^5$ is 3,4-dichlorophenyl.

* * * * *